United States Patent [19]

Strahorn

[11] 4,160,111
[45] Jul. 3, 1979

[54] PROCESS FOR RECOVERING PHENOL FROM AQUEOUS PHENOLIC MIXTURES

[75] Inventor: David F. Strahorn, Oakland, Calif.

[73] Assignee: Chevron Research Company, San Francisco, Calif.

[21] Appl. No.: 801,440

[22] Filed: May 27, 1977

[51] Int. Cl.² ............................................. C07C 37/38
[52] U.S. Cl. ..................................... 568/749; 203/51; 203/54; 203/69
[58] Field of Search ............ 260/621 A, 621 B, 627 R, 260/624 A, 626 R; 203/51, 54, 69; 568/749

[56] References Cited

U.S. PATENT DOCUMENTS

| | | | |
|---|---|---|---|
| 2,286,056 | 6/1942 | Brown | 203/69 |
| 2,322,881 | 6/1943 | Pollock | 202/42 |
| 2,807,654 | 9/1957 | Grimmett et al. | 260/627 R |
| 2,928,882 | 3/1960 | Hall | 260/627 R |
| 3,155,734 | 11/1964 | Merkel | 260/621 R |
| 3,509,028 | 4/1970 | Budd | 203/69 |

*Primary Examiner*—Werren B. Lone
*Attorney, Agent, or Firm*—D. A. Newell; R. H. Davies; D. L. Hagmann

[57] ABSTRACT

An improved process for recovering phenol from phenol-water mixtures by distillation is provided by carrying out the distillation in a manner which avoids the normal phenol-water azeotropic limitation by introducing a ketone-hydrocarbon mixture into the upper section of a fractional distillation column used for the recovery. Mixtures of benzene or lower alkyl substituted benzene with lower ketones are employed in the process.

9 Claims, 2 Drawing Figures

PARTITION COEFFICIENTS⁽¹⁾ FOR BENZENE-2-BUTANONE (B-2-B) MIXTURES (1) $K = \dfrac{\text{WT. \% PHENOL IN B-2-B MIXTURES}}{\text{WT. \% PHENOL IN WATER PHASE}}$

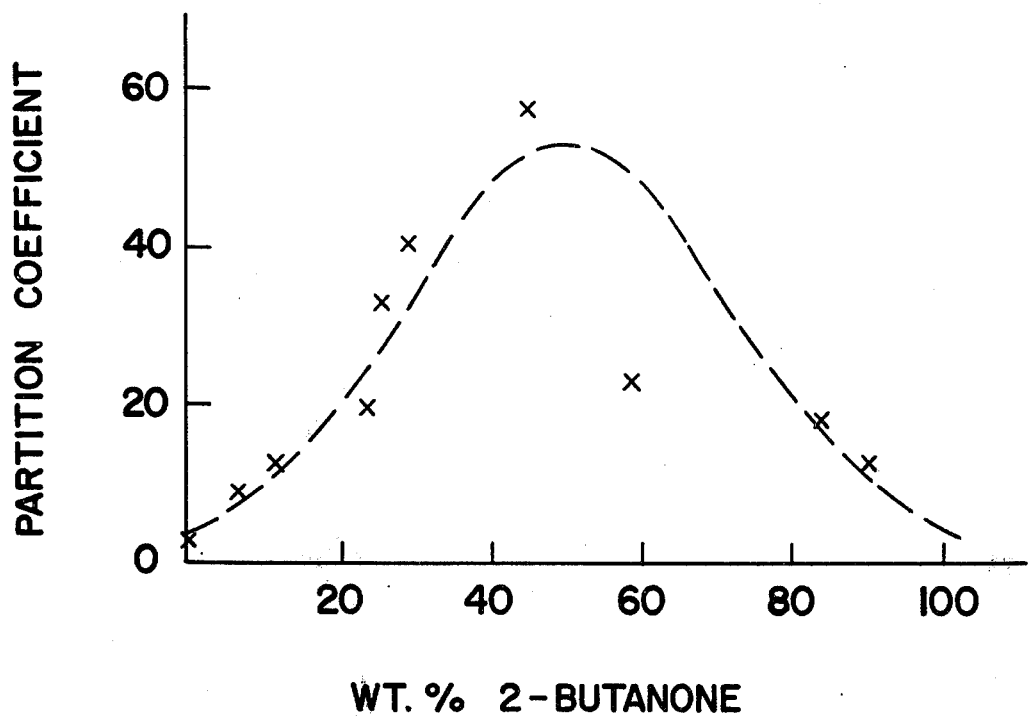
FIG_1

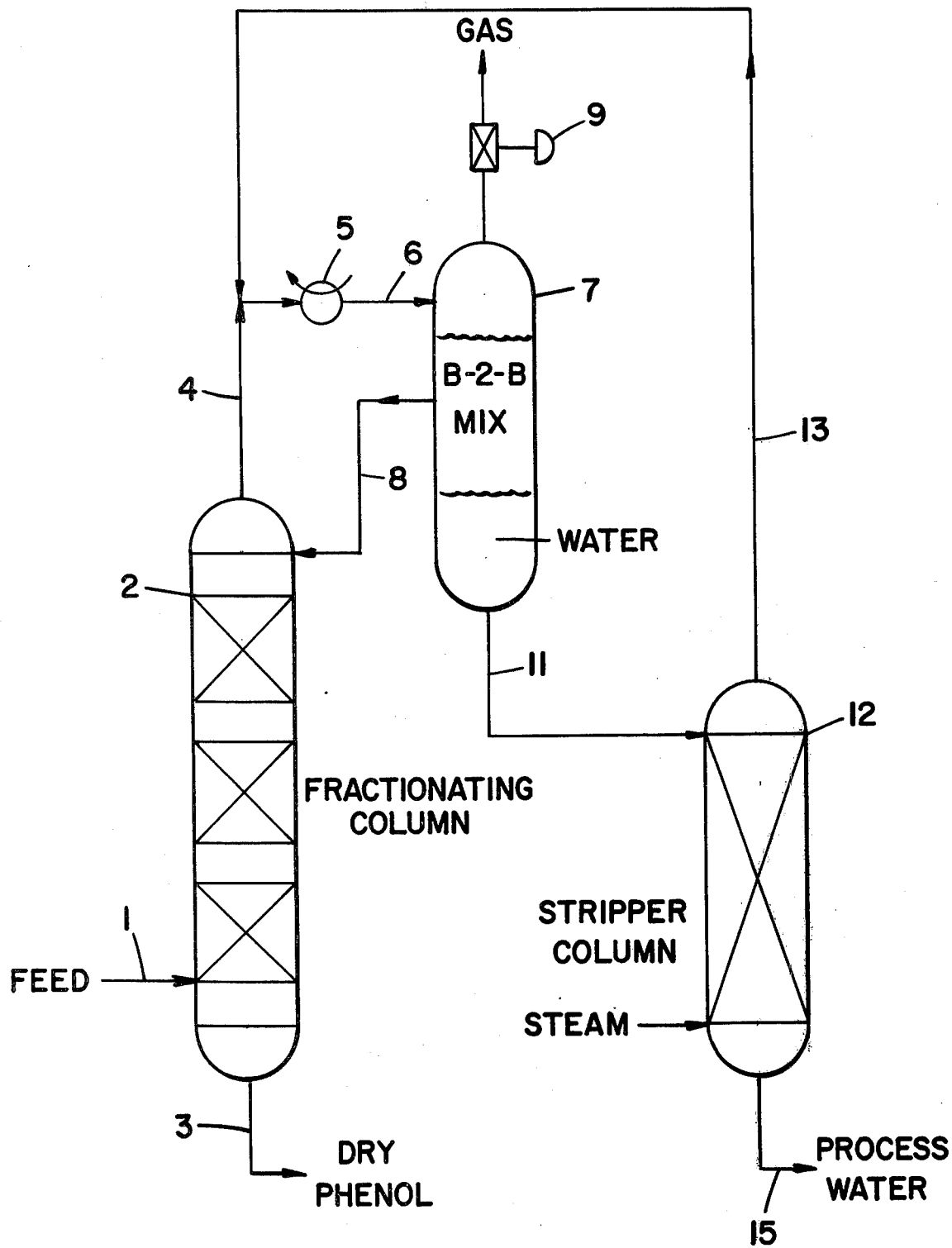
FIG_2

PROCESS FOR RECOVERING PHENOL FROM AQUEOUS PHENOLIC MIXTURES

BACKGROUND OF THE INVENTION

This invention relates to a process for improving the recovery of phenol from aqueous phenolic mixtures by distillation. More particularly, it relates to avoiding the normal phenol-water azeotropic limitation by introducing an organic mixture into the overhead section of a distillation column used to separate phenol-water mixtures. In a more particular aspect of the invention, the organic mixture comprises benzene or lower alkyl substituted benzenes in admixture with lower ketones.

In fractionally distilling phenol-water mixtures in the normal way, the vapor composition in the overhead vapor fraction of the distillation column is limited by the normal phenol-water azeotropic limitation. This is the case because phenol and water form a minimum boiling azeotrope under fractional distillation conditions. This, of course, means that, in general, one cannot satisfactorily separate phenols from water from phenolic water mixtures by a conventional fractional distillation. The separation of materials by fractional distillation is normally a convenient and effective manner in which to separate materials. Consequently, there is a need to improve the normal fractional distillation of phenol-water mixtures in a manner which avoids the azeotropic compositional limitation.

It is an object of this invention to provide an improved distillation process for separating phenol from water. Other objects and the accomplishment thereof will be clear from the description to follow.

SUMMARY OF THE INVENTION

In a process for recovering phenol from an aqueous phenolic mixture by distilling said mixture in a distillation column operating under fractionating conditions, including producing (1) a bottoms fraction comprising phenol, and (2) an overhead vapor fraction having the composition resulting in accordance with the normal phenol-water azeotropic limitation, an improvement is provided comprising:

(1) avoiding said phenol-water compositional limitation by introducing into said upper section, based upon the volume per hour of water in said mixture distilled in said column, an amount of an organic mixture in the range of from about 1 to 20, preferably 5 to 10, volumes per hour, said organic mixture comprising a ketone component and a hydrocarbon component and containing, in parts by weight, for each part of said hydrocarbon component an amount of said ketone component in the range of from about 0.1 to 9 parts, said ketone component containing at least one ketone composed of carbon, hydrogen and oxygen selected from the group consisting of ketones having a carbon-atom content in the range of from 3 to about 7, said hydrocarbon component containing at least about 25 volume percent of at least one aromatic hydrocarbon selected from the group consisting of benzene and lower alkyl substituted benzenes containing less than 4 alkyl substituent groups, with the remainder, if any, comprising an ordinary normally liquid non-aromatic hydrocarbon solvent or fraction thereof; thereby producing an improved overhead vapor fraction which, based upon the water and phenol content thereof, contains less phenol than required to satisfy said normal composition limitation; and (2) withdrawing said improved vapor fraction from said column.

In a yet further aspect of the invention, the aforementioned overhead vapor fraction is cooled, thereby forming an organic phase and an aqueous phase, these phases are separated and at least a portion of the separated organic phase is recycled to the upper section of the distilling column, thereby providing at least a portion of the organic mixture introduced into the overhead section of the column.

In addition to providing a means for avoiding the aforementioned phenol-water azeotrope problem, the organic mixture used in the present process is especially advantageous in that it is an exceptional extraction solvent for removing phenol from water in a liquid-liquid extraction. Consequently, in a phenol-water distillation as herein, a less efficient and hence, costly fractionation in the column is permissible; that is, some phenol may be present in the overhead vapor, because in condensing the overhead vapor fraction from the column, a liquid-liquid extraction is effected. As a practical matter, almost all of the phenol in the overhead fraction is returned to the distillation column in recycled organic mixture and a water raffinate substantially free of phenol is produced.

DESCRIPTION OF THE DRAWINGS

FIG. 1 is a curve showing the enhancement of the phenol extraction coefficient resulting from addition of 2-butanone to benzene in a benzene-water system.

FIG. 2 is a schematic process flow diagram illustrating a preferred embodiment of the invention.

EMBODIMENT

In a preferred embodiment, phenol is recovered from a phenol concentrate which is produced in refining a petroleum stock. A typical such stream is a steam-stripping overhead vapor stream containing, in parts by weight, about 95 parts phenol and about 5 parts water. Referring to FIG. 2, the phenol concentrate is fed via line 1 to fractionating column 2 wherein the bottoms temperature is about 199° C. (390° F.) and the temperature of the overhead vapor section of the column is about 93° C. (200° F.). As a bottoms fraction, dried phenol is withdrawn from the column via line 3 for recovery and use as described, for example, in lube oil processing and the like. The degree of drying achieved in the distillation may vary, ranging from producing anhydrous phenol to phenol containing from 1% to 2% and higher of water, depending upon the contemplated use of the phenol.

Via line 4 an overhead vapor fraction is withdrawn from column 2. This fraction is a mixture of water, benzene, 2-butanone and phenol which is passed into contact with indirect heat exchanger 5 wherein it is cooled and condensed thereby forming an aqueous phase and an organic phase. Indirect heat exchanger 5 may be any suitable unit, for example, an air cooled or a water cooled type heat exchanger or the equivalent. The condensed liquid phases are withdrawn from heat exchanger 5 via line 6 and passed to water separator 7. During the condensation in exchanger 5 and the passage of the liquids through line 6 liquid contacting results providing substantially a single extraction stage. If desirable, and in order to provide the improved liquid-liquid extracting conditions, means for more effective mixing of the condensed phases may be provided. In settler 7, the condensed liquid mixture separates into an upper organic phase comprising 2-butanone, benzene and phenol and a lower water phase which contains less than 1000 ppmw of phenol and from 5-10 weight percent of 2-butanone plus a minor amount of benzene. Via line 8, a portion of the organic phase in settler 7 is withdrawn therefrom and passed to the upper section of fractionating column 2 at a rate to provide a reflux ratio of 10 volumes of the organic mixture per volume of water in the aqueous phenol feed to the column. Depending upon the source, the feed to column 2 may contain a minor amount of a light gas component, for example, propane, ethane, carbon dioxide and the like gases. This component, in the main, accumulates in the overhead void space of separator vessel 7. The venting of this gas from the system via line 10 is controlled by pressure relief valve 9 which is set to maintain a system pressure of about 2 atmospheres absolute.

The separated water phase in vessel 7 contains minor amounts of phenol, 2-butanone and benzene and is withdrawn from vessel 7 via line 11 for delivery to stripper column 12 wherein most of the ketone and benzene therein is steam stripped from the water and returned to the process via line 13. The steam required for the stripping is introduced to column 12 via line 14. Via line 15 the resulting steam stripped water is withdrawn from column 12. This water is suitable for use as feed water for generating steam from steam stripping phenol from a heavy oil.

By "liquid-liquid extracting conditions" as used herein is meant by definition efficient contacting of at least two liquid phases carried out under conditions of temperature and pressure at least sufficient to maintain said liquid phases.

Liquid-liquid extracting conditions are known and used in the extracting art, and such are contemplated for use in the usual way herein. Representative conditions, methods and equipment suitable for use in liquid-liquid extracting for directly contacting separable liquid phases for the purpose of causing transfer of a dissolved substance, for example, phenol as herein, are described in Perry's Chemical Engineer's Handbook, 4th Edition, R. H. Perry, C. H. Chilton and F. D. Kirkpatrick, coeditors, McGraw-Hill Book Company, New York, Sections 21-10 to 21-34. Other leading references are also cited in the above handbook.

EXAMPLES

In a series of runs which were carried out under ambient conditions, that is, at a temperature of about 22° C. and a pressure of 1 atmosphere, the phenol partition coefficients for water and a series of ketone-modified hydrocarbon extracting phases were determined. The extracting phases used in these examples were benzene and a benzene solution containing a range of 2-butanone contents. The results from these runs are shown in FIG. 1. These results illustrate that while benzene or 2-butanone individually exhibit phenol partition coefficients of the relatively low order, for example, of less than about 3 or 5, mixtures of benzene and 2-butanone exhibit, in the partition of phenol between water and the organic extracting medium, partition coefficients which are exceptional. From FIG. 1 it is notable that the addition of but a minor amount of 2-butanone, for example, as little as 10 weight percent, to benzene about doubles the partition coefficient. The coefficient for a 50/50 mixture, relative to that for benzene alone, is larger by about a factor of 20! Similar and advantageous results obtained when lower alkyl substituted benzenes as described above are used in place of benzene and when other ketones as defined above are used in place of 2-butanone. These organic mixtures are also especially suitable for use as the organic mixture which is introduced to the fractionating column of the process herein.

PROCESS PARAMETERS

(A) Organic Mixture

Organic ketone-hydrocarbon mixtures, in general, which exhibit enhanced liquid-liquid phenol distribution coefficients relative to the individual components are effective for use herein for introduction into the overhead section of the distilling column of the process and are contemplated for such use. These mixtures comprise a hydrocarbon component and a ketone component. The hydrocarbon component may vary widely and, in general, must exhibit an appreciable aromatic character, for example, as exhibited by a hydrocarbon mixture having an aromatic hydrocarbon content of at least about 25 volume percent, preferably a content of at least 40 volume percent. More preferably, the hydrocarbon mixture consists essentially of one or more lower aromatic hydrocarbons. As may be noted from FIG. 1, excellent results, in terms of an improved phenol partition coefficient, are achieved in extracting phenol from water when the hydrocarbon component consists essentially of aromatic hydrocarbons. Execellent results are achieved in avoiding the phenolwater azeotropic compositional limitation when the mixture used is a 50/50 mixture of benzene and 2-butanone. However, for practical reasons, including (1) costs and/or (2) the presence in the process feed to the distilling column of a non-aromatic hydrocarbon component, the hydrocarbon component of the organic mixture may be a diluted aromatic hydrocarbon component. Where the hydrocarbon component contains a non-aromatic diluent, the latter may be any known normally liquid non-aromatic hydrocarbon solvent or fraction thereof. Representative such diluents include paraffinic and olefinic petroleum fractions, hexane, hexene, cyclohexane, cyclohexene, heptane, heptene, and the like non-aromatic hydrocarbons, and paraffinic and olefinic components and fractions thereof which are normally present in substantially aromatic product streams ordinarily recovered in a petroleum refinery and as by-products in petroleum refinery process streams.

The aromatic hydrocarbon comprising benzene and alkylsubstituted benzenes and mixtures thereof are preferred for use in the organic mixtures or as components thereof in the present process. Preferably, the aromatic component of the organic mixture contains at least one hydrocarbon selected from the group consisting of benzene and lower alkyl (alkyl groups containing less than 4 carbom atoms) substituted benzenes containing less than 4 alkyl substitutent groups, that is lower aromatic hydrocarbons. Representative aromatic hydrocarbon components include benzene, toluene, xylenes, ethylbenzene, cumene and mixtures thereof. Benzene and toluene are preferred.

(B) Ketone Component Of The Organic Mixture

The ketone component of the organic mixture may be 2-butanone, 2-pentanone, 3-pentanone, acetone and the like ketones and mixtures thereof, that is, the ketone component may be at least one ketone selected from the group consisting of ketones composed of carbon, hydrogen and oxygen and having a carbon atom content in the range from 3 to about 7. In addition to the aforenamed ketones, representative ketones suitable for use herein include cyclohexanone, cyclopentanone, methyl-substituted cyclohexanone, cyclopentanone, ethyl-substituted cyclopentanone, isopropylmethyl, ethylisopropyl and the like acyclic ketones. 2-butanone is a preferred ketone component for use herein.

The amount of ketone component desirably present in the organic mixture varies depending upon a number of factors, including the kind in amount of aromatic hydrocarbon in the hydrocarbon component of the mixture, the particular ketone component employed and the boilup rate of the distilling column. In general, an improved fractionation is obtained when the organic mixture contains for each part by weight of the hydrocarbon component an amount of ketone in the range of from about 0.1 to 9 parts, preferably 0.25 to 4, and more preferably 0.67 to 2 parts.

(C) Temperature And Pressure

The temperatures and pressures employed in the fractional distillation section of the process will, in general, be substantially those normally employed in fractionally distilling phenol-water mixtures. The temperature in the overhead section of the column will, of course, be somewhat modified as a result of the introduction of the organic mixture. These parameters are, of course, interdependent and when one is set the other is also determined. Suitable system pressures range from subatmospheric to superatmospheric pressures, and in general, will be in the range of from about 0.5 to 5 atmospheres.

(D) Organic Mixture To Phenolic Water Volume Ratio

The amount of the organic mixture which must be introduced into the overhead section of the column in order to avoid the normal phenol-water azeotropic compositional limitation varies depending, in the main, upon the water content of the feed to the distillation column and upon the particular organic mixture being used. In general, for each volume of water in the feed, the introduction into the overhead section of the column of an amount of the organic mixture in the range of from about 1 to 20, preferably 5 to 10 volumes will be effective in avoiding the azeotropic compositional limitation.

It is apparent that many widely different embodiments of this invention may be made without departing from the scope and spirit thereof; and, therefore, it is not intended to be limited except as indicated in the appended claims.

What is claimed is:

1. In a method for separating phenol from water wherein a phenol-water mixture is distilled in a distillation column to form a liquid fraction comprising phenol and a vapor fraction containing water and phenol in concentrations in accordance with the normal phenol-water azeotrope, the improvement comprising:
   fractionating said phenol-water mixture in the presence of an organic mixture comprising a ketone component and a hydrocarbon component, said organic mixture being present at a concentration of from 1 to 20 volumes per volume of water in said phenol-water mixture, said organic mixture including from about 0.1 to 9 parts, by weight, of said ketone component for each part of said hydrocarbon component, said ketone component comprising at least one ketone containing from 3 to 7 carbon atoms, and said hydrocarbon component comprising from about 25 volume percent to 100 volume percent of at least one aromatic hydrocarbon selected from the group consisting of benzene and lower alkyl substituted benzenes containing less than 4 alkyl substituent groups and from 0 volume percent to about 25 volume percent of a normally liquid non-aromatic hydrocarbon solvent, whereby the concentration of phenol in said vapor fraction is reduced.

2. A process as defined in claim 1 further including the steps of (1) forming an organic phase and an aqueous phase by condensing said vapor fraction, (2) separating said phases and (3) using at least a portion of said organic phase as at least a portion of said organic mixture.

3. A process as defined in claim 1 wherein (1) said organic mixture is present in an amount between 1 and 5 volumes per volume of water in said phenol-water mixture, (2) said ketone component is present in said organic mixture in a concentration of from about 0.25 to 4 volumes per volume of said hydrocarbon component, and (3) said hydrocarbon component comprises at least 25 volume percent of said organic mixture.

4. A process as defined in claim 1 wherein (1) said ketone component consists essentially of 2-butanone and (2) said aromatic hydrocarbon component is selected from the group consisting of benzene, toluene and mixtures thereof.

5. A process as defined in claim 4 wherein said ketone component is present in said organic mixture in a concentration in the range of from about 0.25 to 4 parts per part of said hydrocarbon component.

6. A process as defined in claim 1 wherein said organic mixture contains about equal parts of said ketone component and said aromatic component.

7. A process as defined in claim 2 wherein said aqueous phase contains a minor amount of said hydrocarbon and ketone components and further including the steps of (1) separating at least a portion of said contained components, from said aqueous phase by steam stripping said aqueous phase, thereby producing a vapor phase containing said stripped components, and (2) introducing at least a portion of said vapor phase to said column.

8. A process as defined in claim 1 wherein (a) said phenol-water mixture comprises, by weight, about 95 parts phenol and about 5 parts water; (b) said phenol-water mixture is distilled at a pressure of about 2 atmospheres absolute, a bottoms temperature of about 199° C. and an overhead vapor section temperature of about 93° C. in said column; and (c) said organic mixture comprises 2-butanone and benzene and further including the steps of (1) condensing said vapor fraction to form an upper organic phase comprising 2-butanone, benzene and phenol and a lower water phase containing from 5 to 10 weight percent of 2-butanone, less than about 1000 ppmw of phenol and a minor amount of benzene; and (2) introducing at least a portion of said organic phase to said column, thereby providing a reflux ratio of about 10 volumes of said organic mixture per volume of water in said phenol-water mixture.

9. A process as defined in claim 8 further including the steps of removing at least a portion of said 2-butanone present in said lower water phase by steam stripping and introducing the resulting vapor into said column.

* * * * *